(12) United States Patent
Casas

(10) Patent No.: US 11,389,639 B2
(45) Date of Patent: Jul. 19, 2022

(54) ANTI-THROMBUS SURFACE POTENTIAL CERAMIC ELEMENT

(71) Applicant: HeartWare, Inc., Miami Lakes, FL (US)

(72) Inventor: Fernando Casas, Miami Lakes, FL (US)

(73) Assignee: HEARTWARE, INC., Miami Lakes, FL (US)

( * ) Notice: Subject to any disclaimer, the term of this patent is extended or adjusted under 35 U.S.C. 154(b) by 0 days.

(21) Appl. No.: 15/946,892

(22) Filed: Apr. 6, 2018

(65) Prior Publication Data

US 2018/0303989 A1 Oct. 25, 2018

Related U.S. Application Data

(60) Provisional application No. 62/489,629, filed on Apr. 25, 2017.

(51) Int. Cl.
| | | |
|---|---|---|
| *A61M 1/10* | (2006.01) | |
| *A61M 60/422* | (2021.01) | |
| *A61M 60/148* | (2021.01) | |
| *A61M 60/818* | (2021.01) | |
| *A61M 60/857* | (2021.01) | |
| *F04D 7/04* | (2006.01) | |
| *F04D 13/06* | (2006.01) | |
| *A61M 60/82* | (2021.01) | |
| *A61M 60/824* | (2021.01) | |

(52) U.S. Cl.
CPC ........ *A61M 60/422* (2021.01); *A61M 60/148* (2021.01); *A61M 60/818* (2021.01); *A61M 60/857* (2021.01); *A61M 60/82* (2021.01); *A61M 60/824* (2021.01); *F04D 7/04* (2013.01); *F04D 13/0633* (2013.01)

(58) Field of Classification Search
CPC .................................. A61M 1/10; A61M 1/12
See application file for complete search history.

(56) References Cited

U.S. PATENT DOCUMENTS

| | | | |
|---|---|---|---|
| 5,041,132 A * | 8/1991 | Miyata | A61M 1/1046 310/316.02 |
| 5,092,878 A | 3/1992 | Miyata | |
| 5,399,074 A | 3/1995 | Nose et al. | |
| 5,713,730 A | 2/1998 | Nose et al. | |

(Continued)

FOREIGN PATENT DOCUMENTS

| | | |
|---|---|---|
| CN | 101371041 A | 2/2009 |
| CN | 104768589 A | 7/2015 |

OTHER PUBLICATIONS

International Search Report and Written Opinion dated Jun. 27, 2018 for corresponding International Application No. PCT/US2018/026488; International Filing Date: Apr. 6, 2018 consisting of 11-pages.

(Continued)

*Primary Examiner* — Matthew W Schall
(74) *Attorney, Agent, or Firm* — Shumaker & Sieffert, P.A.

(57) ABSTRACT

An implantable blood pump comprising a housing. At least one stator is disposed within the housing. A rotor is disposed within the housing, the at least one stator being configured to rotate the rotor when current is applied to the stator. At least one at least partially piezoelectric disk is disposed within the housing.

15 Claims, 4 Drawing Sheets

(56) References Cited

U.S. PATENT DOCUMENTS

| | | |
|---|---|---|
| 6,158,984 A | 12/2000 | Cao et al. |
| 6,688,861 B2 | 2/2004 | Wampler |
| 7,575,423 B2 | 8/2009 | Wampler |
| 7,976,271 B2 | 7/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 2007/0280841 A1 | 12/2007 | LaRose et al. |
| 2009/0234447 A1 | 9/2009 | LaRose et al. |
| 2015/0051438 A1 | 2/2015 | Taskin |

OTHER PUBLICATIONS

China National Intellectual Property Administration, Notice On The First Office Action for corresponding CN Application No. 201880027201.7, dated Jun. 21, 2021, 18 pages.

Second Office Action, and translation thereof, from counterpart Chinese Application No. 201880027201.7 dated Nov. 29, 2021, 12 pp.

* cited by examiner

ANTI-THROMBUS SURFACE POTENTIAL CERAMIC ELEMENT

CROSS-REFERENCE TO RELATED APPLICATION

This application is related to and claims priority to U.S. Provisional Patent Application Ser. No. 62/489,629, filed Apr. 25, 2017, entitled ANTI-THROMBUS SURFACE POTENTIAL CERAMIC ELEMENT, the entirety of which is incorporated herein by reference.

STATEMENT REGARDING FEDERALLY SPONSORED RESEARCH OR DEVELOPMENT n/a

TECHNICAL FIELD

This disclosure relates to a blood pump with integrated anti-thrombus elements.

BACKGROUND

Implantable blood pumps used as mechanical circulatory support devices or "MCSDs" include a pumping mechanism to move blood from the heart out to the rest of the body. The pumping mechanism may be a centrifugal flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated herein in its entirety. In operation, the blood pump draws blood from a source such as the right ventricle, left ventricle, right atrium, or left atrium of a patient's heart and impels the blood into an artery such as the patient's ascending aorta or peripheral artery.

In an exemplary HVAD® pump, an impeller is positioned within a housing having an upstream inflow cannula and a downstream outlet. The impeller is configured to rotate along an axis defined by the rotor and to impel blood upstream from the inflow cannula downstream to the outlet. In such a configuration, the impeller pumps blood in a direction substantially perpendicular to the axis about which it rotates. Dual stators are included in the pump, one upstream of the impeller and one downstream from the impeller and are each configured to rotate the impeller to impel blood. Disposed between the impeller and each respective stator is a non-ferromagnetic ceramic disk that separates the respective stator from the impeller and provides a smooth surface to pump blood. However, owing to the small gap between each ceramic disk and the impeller, there is the possibility that particles may become lodged between the impeller and the ceramic disk.

SUMMARY

Some embodiments advantageously provide an implantable blood pump comprising a housing. At least one stator is disposed within the housing. A rotor is disposed within the housing, the at least one stator being configured to rotate the rotor when current or voltage is applied to the stator. At least one at least partially piezoelectric disk is disposed within the housing.

In another aspect of this embodiment, the at least one at least partially piezoelectric element is at least one from the group consisting of a ceramic disk and a ceramic tube.

In another aspect of this embodiment, the at least one at least partially piezoelectric element is in communication with a power source.

In another aspect of this embodiment, the at least one at least partially piezoelectric element includes a plurality of piezoelectric zones separated by at least one non-piezoelectric zone.

In another aspect of this embodiment, the power source is configured to selectively apply a voltage and induce a current to each of the plurality of piezoelectric zones.

In another aspect of this embodiment, the at least one at least partially piezoelectric element is configured to vibrate when the power source applies a voltage and induces a current to the at least one at least partially piezoelectric element.

In another aspect of this embodiment, the at least one piezoelectric element generates a surface potential during operation of the blood pump.

In another aspect of this embodiment, the at least one at least partially piezoelectric element includes a plurality of piezoelectric zones separated by at least one non-piezoelectric zone.

In another aspect of this embodiment, the power source is configured to regulate the surface potential of the plurality of piezoelectric zones.

In another aspect of this embodiment, the at least one at least partially piezoelectric element is entirely piezoelectric.

In another embodiment, an implantable blood pump includes a housing having an upstream end and a downstream end. A first stator is disposed within the housing. A rotor is disposed within the housing, the first stator being is configured to rotate the rotor when a voltage is applied to the first stator. The rotor is positioned within the housing downstream from the first stator. A first at least partially piezoelectric disk is disposed within the housing, the first at least partially piezoelectric disk is disposed between the first stator and the rotor. A second stator is disposed within the housing downstream from the rotor, the second stator is configured to rotate the rotor when a voltage is applied to the second stator. A second at least partially piezoelectric disk downstream is disposed between the second stator and the rotor.

In another aspect of this embodiment, the at least one at least partially piezoelectric element is in communication with a power source exterior to the housing.

In another aspect of this embodiment, the first at least partially piezoelectric disk and the second at least partially piezoelectric disk are composed of one from the group consisting of a ceramic disk and a ceramic tube.

In another aspect of this embodiment, the first at least partially piezoelectric disk and the second at least partially piezoelectric disk include a plurality of piezoelectric zones separated by at least one non-piezoelectric zone.

In another aspect of this embodiment, the power source is configured to selectively apply a voltage and induce a current to each of the plurality of piezoelectric zones.

In another aspect of this embodiment, the first at least partially piezoelectric disk and the second at least partially piezoelectric disk are configured to vibrate when the power source applies a voltage and induces a current to the at least one at least partially piezoelectric element.

In another aspect of this embodiment, the first at least partially piezoelectric disk and the second at least partially piezoelectric disk generate a surface potential during operation of the blood pump.

In another aspect of this embodiment, the first at least partially piezoelectric disk and the second at least partially piezoelectric disk include a plurality of piezoelectric zones separated by at least one non-piezoelectric zone.

In another aspect of this embodiment, the power source is configured to regulate the surface potential of the plurality of piezoelectric zones.

In another embodiment, a method of clearing thrombus from an implantable blood pump includes applying a voltage and inducing a current to an at least partially piezoelectric material disposed within the implantable blood pump, the blood pump having a rotor and at least one stator configured to rotate the rotor, the at least partially piezoelectric material disposed between the rotor and the at least one stator.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
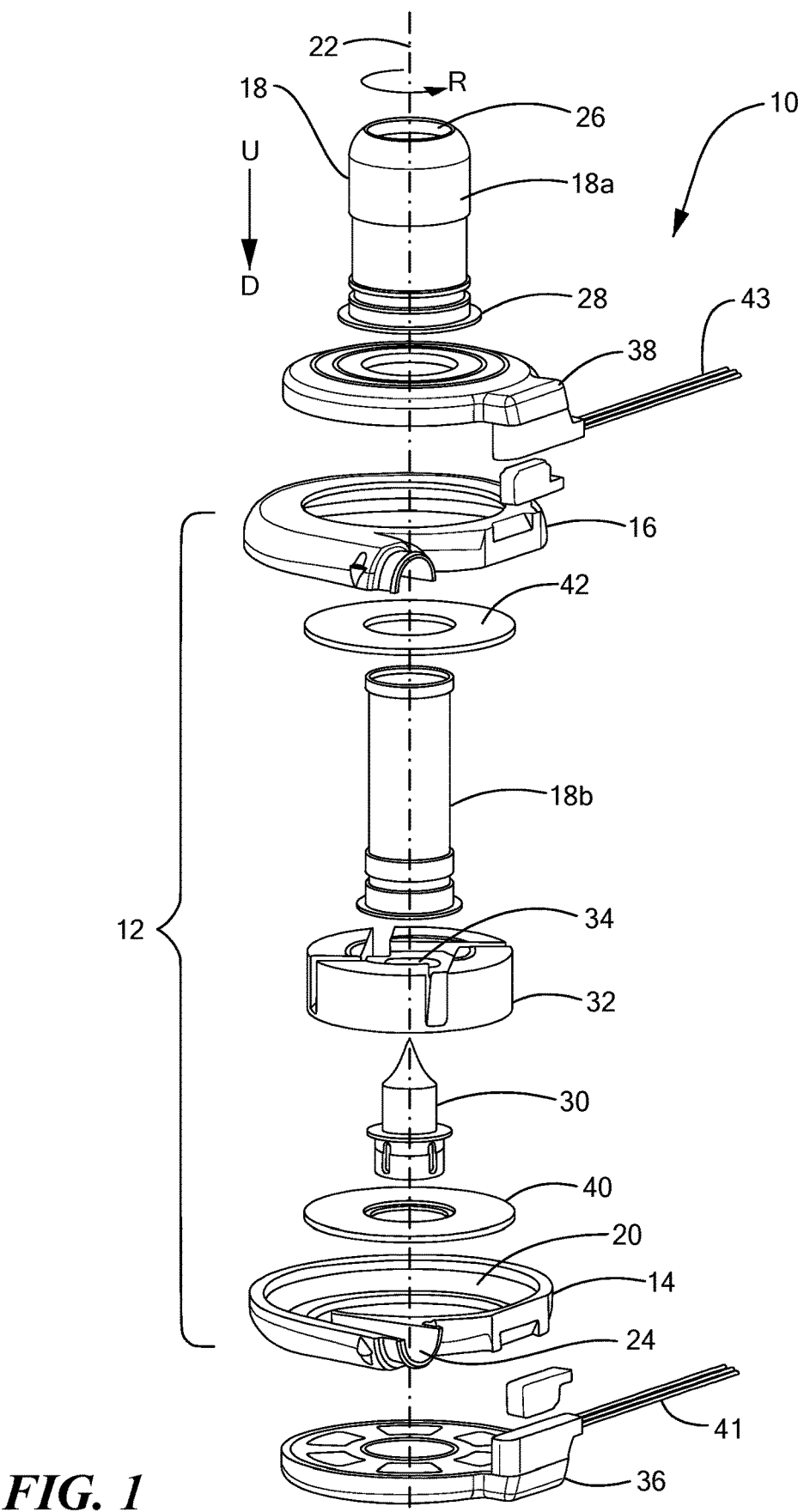
FIG. 1 is an exploded view of an exemplary blood pump constructed in accordance of the principles of the present application.

Referring now to the drawings in which like reference designators refer to like elements there is shown in FIG. 1 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

Figure 2:
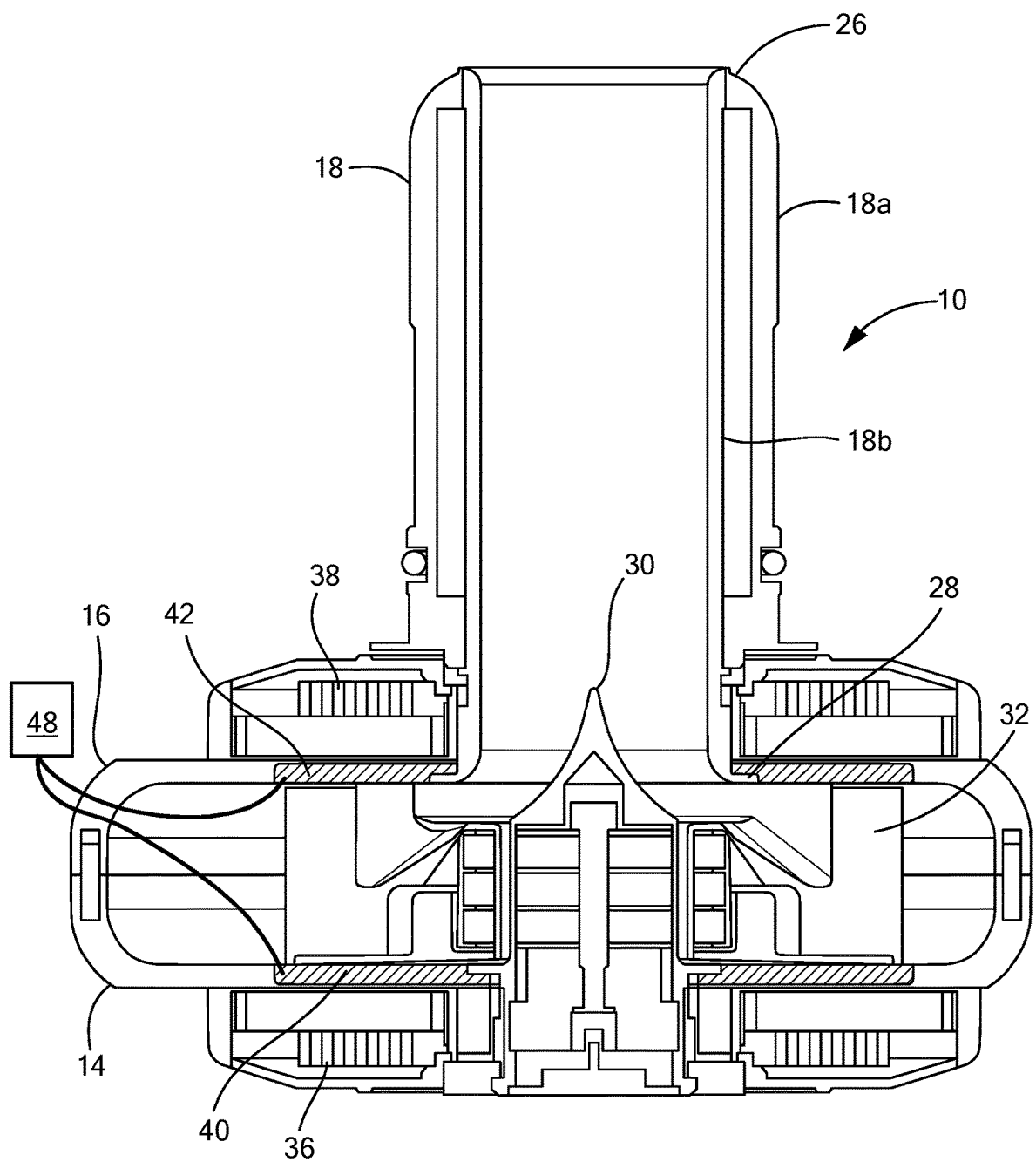
FIG. 2 is cross-sectional view of the assembled blood pump shown in FIG. 1.
Figure 3:
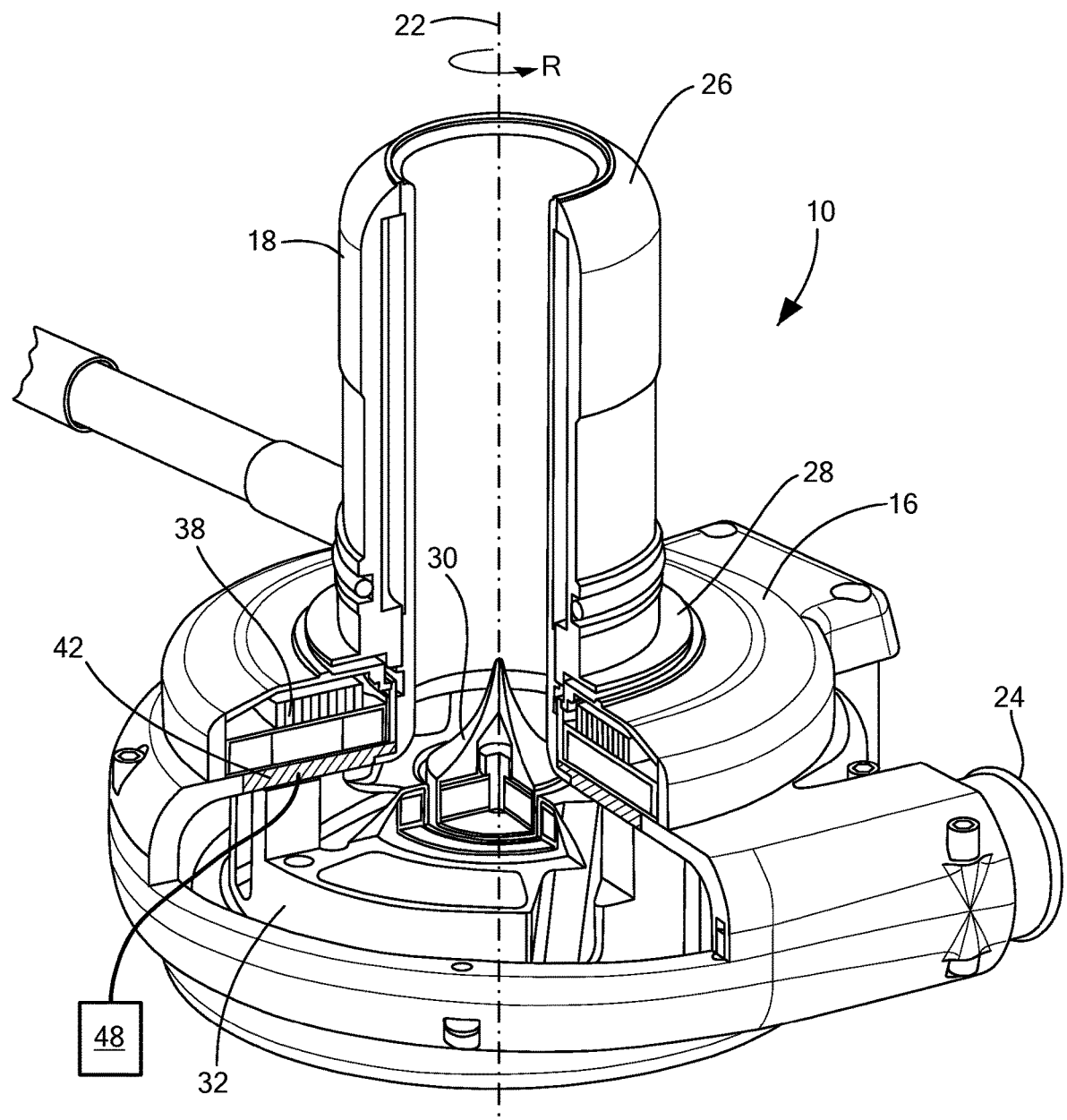
FIG. 3 is a slice cross-sectional view of the blood pump shown in FIG. 2.

Referring now to FIGS. 1 and 2, the inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc-shaped ferromagnetic rotor 32 with a central hole 34 is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 (FIG. 1) are provided on the first stator 36 and the second stator 38 respectively for connecting the coils to a source of power such as a controller (not shown). The controller is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation, as discussed in more detail below. The general arrangement of the components described above may be similar to the blood pump 10 used in the MCSD sold under the designation HVAD by Heart-Ware, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 4:
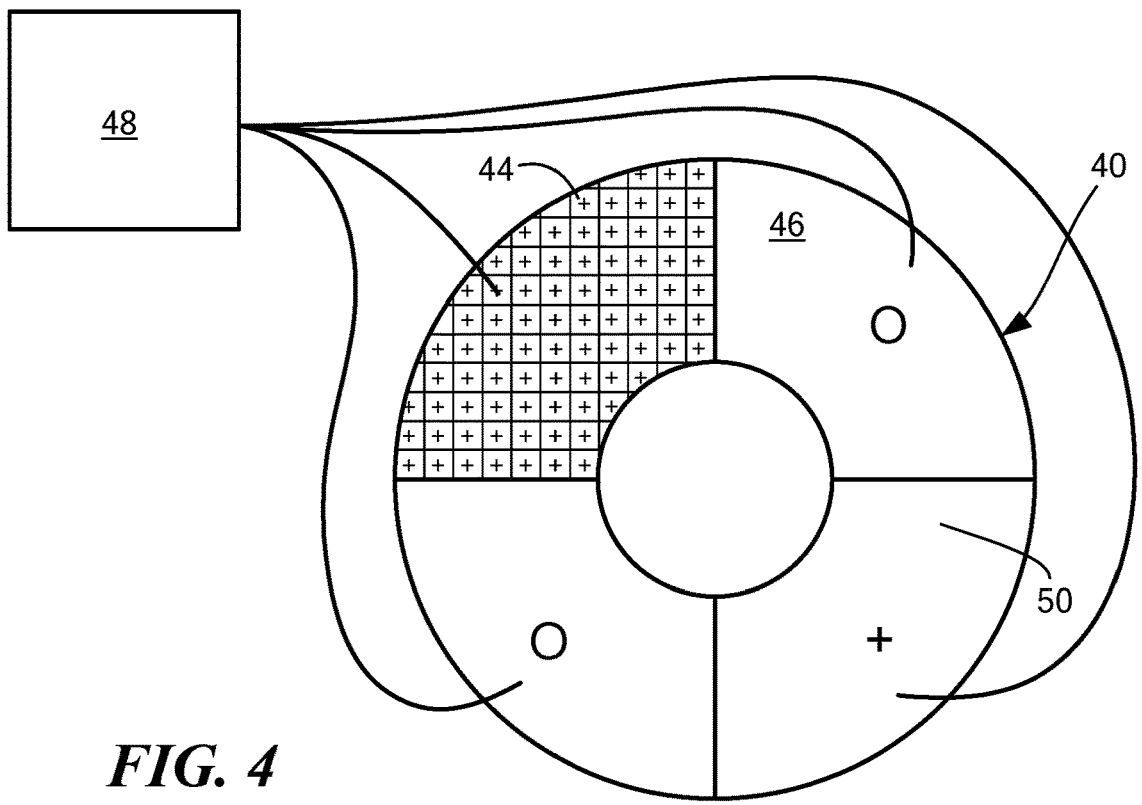
FIG. 4 is a top view of a piezoelectric disk shown in FIG. 1.
Figure 5:
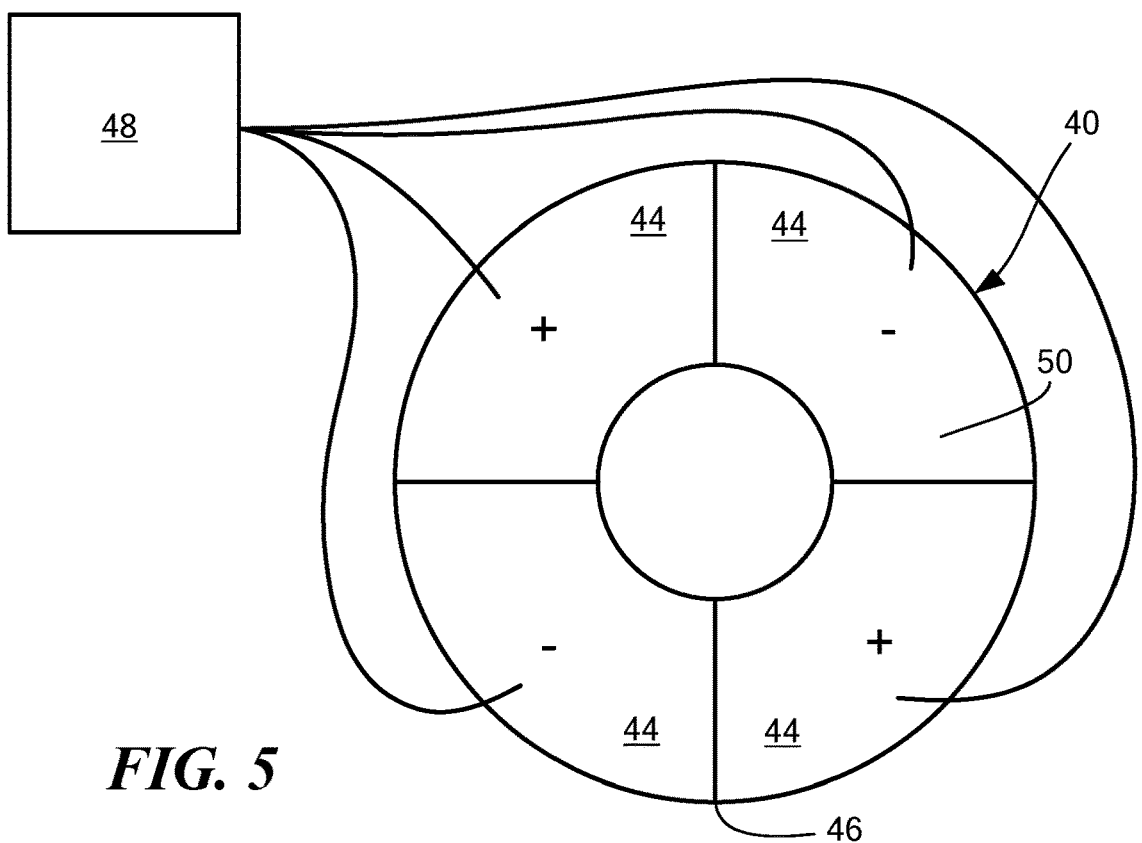
FIG. 5 is a top view of another configuration of the piezoelectric disk shown in FIG. 4.

Referring to FIGS. 1-5, a first non-ferromagnetic disk 40 may be disposed within the first portion 14 downstream from the rotor 32 between the first stator 36 and the rotor 32, and a second non-ferromagnetic disk 42 may be disposed upstream from the rotor 32 within the second portion 16 between the second stator 38 and the rotor 32. The first and second disks 40 and 42 may be at least partially composed of a piezoelectric material, for example, a piezoelectric ceramic, configured to vibrate, generate an electric potential, and/or a combination of both in the presence of voltage and/or current. The first and second disks 40 and 42 may be entirely or at least partially composed of a piezoelectric ceramic either by being coated with a piezoelectric material or having portions including piezoelectric material. For example, in one configuration, the first and/or second disks 40 and 42 may define a plurality of zones 44 composed of piezoelectric material separated by at least one non-piezoelectric zone 46. The size of the non-piezoelectric zone 46 may vary with particular application. For example, as shown in FIG. 4, the plurality of zones 44 are equal in size to the at least one non-piezoelectric zone 46. Thus, only a portion of the first and second disks 40 and 42 may be piezoelectric. As shown in FIG. 5, the plurality of zones 44 are sized to encompass substantially the entirety of each respective disk first and second disks 40 and 42. Any combination and size of piezoelectric zones 44 and non-piezoelectric zones 46 may be encompassed either of both of disks 40 and 42.

The disks 40 and/or 42 and their associated plurality of zones 44 may be electrically coupled to a voltage source 48 configured to apply an electric potential to each of the plurality of zones 44 simultaneously and/or sequentially and induce a current in the disks 40 and/or 42. The voltage source 48 may be the same voltage source as the voltage source configured to supply power to the first stator 36 and the second stator 38 or may be a separate voltage source. For example, the conductors 41 and 43 may be split to connect to the plurality of zones 44 or one or more separate conductors may connect the plurality of zones 44 to provide for a particular surface potential. For example, as shown in FIG. 4, the plurality of zones 44 are applied a positive electric potential as indicated by the "+" sign. The non-piezoelectric zones 46 are indicted by "0" to represent a neutral charge. In other configurations, as shown in FIG. 5, the piezoelectric zones 44 may be negatively charged or may alternate between positive and negative charge. In one configuration, the application of a voltage potential causes disks 40 and 42 to vibrate, generate an electric potential, or both, which may have the effect to dislodge any thrombus that may have developed on the surface of the disks 40 and 42 respectively. The surface potential from the voltage source 48 may be applied intermittently to each disk 40 and 42 simultaneously or sequentially. For example, the voltage source 48 may be programmed to apply a voltage, and thus deliver an electric current, at a predetermined interval, for example, every 5 seconds, although any interval may be selected. The voltage source 48 may be further programmed to selectively apply a voltage to each of the plurality of zones 44 simultaneously or sequentially, such that each zone 44 may be applied a voltage potential independently of the other zones 44 or simultaneously with the other zones 44. Moreover, as shown in FIG. 5, each zone 44 may have the same or potential, the opposite potential as an adjacent zone, or a greater surface potential than an adjacent zone. For example, one zone 44 of one or both of the disks 40 and 42 may have a surface potential of a predetermined voltage and other zones 44 may have a surface potential that is half, twice, three times, etc. of the predetermined voltage. Thus, patterns of vibrating zones 44 or zones 44 with different electric potentials, may be created of different intensity to effectively wash thrombus from the surface of the disks 40 and/or 42. The disks 40 and/or 42 may further exhibit the piezoelectric effect in that the disks 40 and/or 42 may generate a surface potential in response to vibrating as an applied mechanical stress. For example, based on the thickness, size, and other material properties, the piezoelectric disks 40 and/or 42 may vibrate during operation of the pump which causes surface potentials to be created on the surface of the disks 40 and/or 42. The generated surface potentials may be configured to repel thrombus away from the disks 40 and/or 42. The disks 40 and/or 42 may not necessarily be uniform in shape and thickness and thus may exhibit different piezoelectric effects which may be utilized to effectively reduce thrombus. For example, certain zones 44 may generate larger potentials than other zones thus creating a sweeping effect to wash thrombus or other particles from the surface of the disks 40 and/or 42.

In one configuration, the disks 40 and/or 42 may include a microelectromechanical system (MEMS) device 50 on the surface of the disks 40 and/or 42 facing the their respective stators 36 and 38 configured to either selectively apply a surface potential or receive a charge from the disks 40 and/or 42. For example, the MEMS device 50 may be a sticker that is adhered to the disks 40 and/or 42, or alternatively may be attached or etched into the surface of each disk 40 and/or 42. The MEMS device 50 may be coupled to the voltage source 48 and may further include a wireless transmitter and receiver (not shown) such that the plurality of zones 44 may include independently controllable arrays within each zone 44. For example, as shown in FIG. 4, the MEMS device 50 defines a grid of independently controllable portions that may be activated in series, simultaneously, or with a predetermined pattern, to cause a desired piezoelectric effect. The MEMS device 50 could be disposed on a portion of the disks 40 and/42 or encompass the entire disks 40 and/or 42.

Although the above embodiments are described with respect to a dual stator system, it is contemplated that piezoelectric tubes may be used in the manner describe herein in axial flow pumps having a single stator as described in U.S. Pat. No. 8,007,254 and U.S. Patent Application Publication No. 2015/0051438 A1, sold under the designation MVAD by Heartware, Inc., assignee of the present application. For example, axial flow pumps, such as MVAD include a non-piezoelectric ceramic tube within which the impeller rotates. The non-piezoelectric tube may include the piezoelectric properties as described above in any combination or functionality of the piezoelectric disks 40 and 42.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following Embodiments.

What is claimed is:

1. An implantable blood pump, comprising:
   a housing;
   at least one stator disposed within the housing;
   a rotor disposed within the housing, the at least one stator being configured to rotate the rotor when current is applied to the stator;
   at least one at least partially piezoelectric element disposed within the housing and separated from and disposed between the at least one stator and the rotor; and
   the at least one at least partially piezoelectric element includes a plurality of piezoelectric zones separated by at least one non-piezoelectric zone.

2. The blood pump of claim 1, wherein the at least one at least partially piezoelectric element is one from the group consisting of a ceramic disk and a ceramic tube.

3. The blood pump of claim 1, wherein the at least one at least partially piezoelectric element is in communication with a power source.

4. The blood pump of claim 3, wherein the power source is configured to selectively apply a voltage and induce a current to each of the plurality of piezoelectric zones.

5. The blood pump of claim 3, wherein the at least one at least partially piezoelectric element is configured to vibrate when the power source applies a voltage and current is induced in at least one at least partially piezoelectric element.

6. The blood pump of claim 3, wherein the at least one piezoelectric element generates a surface potential during operation of the blood pump.

7. The blood pump of claim 2, wherein the power source is configured to regulate the surface potential of the plurality of piezoelectric zones.

8. The blood pump of claim 1, wherein the at least one at least partially piezoelectric element is entirely piezoelectric.

9. An implantable blood pump, comprising:
a housing having an upstream end and a downstream end;
a first stator disposed within the housing;
a rotor disposed within the housing, the first stator being configured to rotate the rotor when a voltage is applied to the first stator, the rotor being positioned within the housing downstream from the first stator; and
a first at least partially piezoelectric disk disposed within the housing and separated from the first stator, the first at least partially piezoelectric disk being disposed between the first stator and the rotor; and
a second stator disposed within the housing downstream from the rotor, the second stator being configured to rotate the rotor when a voltage is applied to the second stator;
a second at least partially piezoelectric disk downstream disposed between the second stator and the rotor and separated from the second stator; and
the first at least partially piezoelectric disk and the second at least partially piezoelectric disk each include a plurality of piezoelectric zones separated by at least one non-piezoelectric zone.

10. The blood pump of claim 9, wherein the first at least partially piezoelectric disk and the second at least partially piezoelectric disk are in communication with a power source exterior to the housing.

11. The blood pump of claim 10, wherein the power source is configured to selectively apply a voltage and induce a current to each of the plurality of piezoelectric zones.

12. The blood pump of claim 10, wherein the first at least partially piezoelectric disk and the second at least partially piezoelectric disk are configured to vibrate when the power source applies a voltage and current is induced in the first at least partially piezoelectric disk and the second at least partially piezoelectric disk.

13. The blood pump of claim 10, wherein the first at least partially piezoelectric disk and the second at least partially piezoelectric disk generate a surface potential during operation of the blood pump.

14. The blood pump of claim 10, wherein the power source is configured to regulate the surface potential of the plurality of piezoelectric zones.

15. The blood pump of claim 1, wherein the at least one at least partially piezoelectric element is a tube.

\* \* \* \* \*